United States Patent
Jonckers et al.

(10) Patent No.: US 8,481,510 B2
(45) Date of Patent: Jul. 9, 2013

(54) URACYL SPIROOXETANE NUCLEOSIDES

(75) Inventors: Tim Hugo Maria Jonckers, Edegem (BE); Pierre Jean-Marie Raboisson, Rosieres (BE); Koen Vandyck, Paal-Beringen (BE); Steven Maurice Van Hoof, Merelbeke (BE); Lili Hu, Mechelen (BE); Abdellah Tahri, Anderlecht (BE)

(73) Assignees: Janssen Products, LP, Horsham, PA (US); Medivir AB, Huddinge (SE)

( * ) Notice: Subject to any disclaimer, the term of this patent is extended or adjusted under 35 U.S.C. 154(b) by 0 days.

(21) Appl. No.: 13/319,735

(22) PCT Filed: May 11, 2010

(86) PCT No.: PCT/EP2010/056438
§ 371 (c)(1),
(2), (4) Date: Nov. 10, 2011

(87) PCT Pub. No.: WO2010/130726
PCT Pub. Date: Nov. 18, 2010

(65) Prior Publication Data
US 2012/0065156 A1   Mar. 15, 2012

(30) Foreign Application Priority Data
May 14, 2009  (EP) .................................. 09160215

(51) Int. Cl.
*A01N 43/04* (2006.01)
*A61K 31/70* (2006.01)
*C07H 1/00* (2006.01)

(52) U.S. Cl.
USPC ............ 514/50; 514/49; 536/28.1; 536/28.53

(58) Field of Classification Search
None
See application file for complete search history.

(56) References Cited

FOREIGN PATENT DOCUMENTS

| WO | WO 2006/012078 A | 2/2006 |
|----|------------------|--------|
| WO | WO 2007/020193 A | 2/2007 |
| WO | WO 2007/095269 A | 8/2007 |

OTHER PUBLICATIONS

Babu et al., Org. Biomol. Chem., vol. 1, pp. 3514-3526, 2003.*
Babu, B.R., et al., "2'-Spiro Ribo- and Arabinonucleosides: Synthesis, Molecular Modeling and Incorporation into Oligodeoxynucleotides", Org. Biomol. Chem., vol. 1, pp. 3514-3526, (2003).
Krieger, N., et al., "Enhancement of Hepatitis C Virus RNA Replication by Cell Culture-Adaptive Mutations", Journal of Virology, vol. 75, No. 10, pp. 4614-4624, (2001).
Li, N., et al., "Efficient Synthesis of Methyl 3,5-Di-*O*-benzyl-α-D-Ribofuranoside and Application to the Synthesis of 2'-*C*-β-Alkoxymethyluridines", Organic Letters, vol. 9, No. 16, pp. 3009-3012, (2007).
Lohmann, V., et al., "Replication of Subgenomic Heatitis C Virus RNAs in a Hepatoma Cell Line", Science, vol. 285, pp. 110-113 (1999).

* cited by examiner

*Primary Examiner* — Traviss C McIntosh, III
(74) *Attorney, Agent, or Firm* — Andrea Jo Kamage

(57) ABSTRACT

Compounds of the formula I:

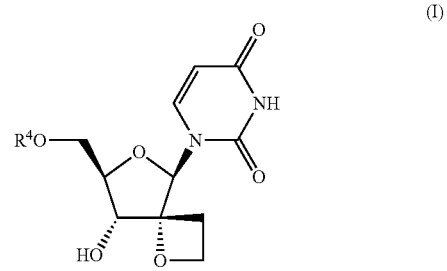

including any possible stereoisomers thereof, wherein:
$R^4$ is a monophosphate, diphosphate or triphosphate ester; or $R^4$ is

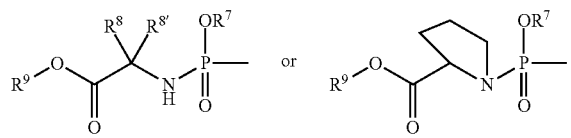

$R^7$ is optionally substituted phenyl, optionally substituted naphthyl, or optionally substituted indolyl;
$R^8$ and $R^{8'}$ are hydrogen, $C_1$-$C_6$alkyl, benzyl, or phenyl; or $R^8$ and $R^{8'}$ form $C_3$-$C_7$cycloalkyl;
$R^9$ is $C_1$-$C_{10}$alkyl, $C_3$-$C_7$cycloalkyl, phenyl or phenyl-$C_1$-$C_6$alkyl, wherein the phenyl moiety in phenyl or phenyl-$C_1$-$C_6$alkyl is optionally substituted;
or a pharmaceutically acceptable salt or solvate thereof;
pharmaceutical formulations and the use of compounds I as HCV inhibitors.

15 Claims, No Drawings

URACYL SPIROOXETANE NUCLEOSIDES

BACKGROUND OF THE INVENTION

This invention relates to uracyl spirooxetane nucleosides that are inhibitors of the hepatitis C virus (HCV).

HCV is a single stranded, positive-sense RNA virus belonging to the Flaviviridae family of viruses in the hepacivirus genus. The NS5B region of the RNA polygene encodes a RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations. There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapy is based on (pegylated) interferon-alpha (IFN-α) in combination with ribavirin. This combination therapy yields a sustained virologic response in more than 40% of patients infected by genotype 1 HCV and about 80% of those infected by genotypes 2 and 3. Beside the limited efficacy against HCV genotype 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosing regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5B RdRp is essential for replication of the single-stranded, positive sense, HCV RNA genome. This enzyme has elicited significant interest among medicinal chemists. Both nucleoside and non-nucleoside inhibitors of NS5B are known. Nucleoside inhibitors can act as a chain terminator or as a competitive inhibitor, or as both. In order to be active, nucleoside inhibitors have to be taken up by the cell and converted in vivo to a triphosphate. This conversion to the triphosphate is commonly mediated by cellular kinases, which imparts additional structural requirements on a potential nucleoside polymerase inhibitor. In addition this limits the direct evaluation of nucleosides as inhibitors of HCV replication to cell-based assays capable of in situ phosphorylation.

Several attempts have been made to develop nucleosides as inhibitors of HCV RdRp, but while a handful of compounds have entered clinical development, none have proceeded all the way to registration. Amongst the problems which HCV-targeted nucleosides have encountered to date are toxicity, mutagenicity, lack of selectivity, poor efficacy, poor bioavailability, sub-optimal dosage regimes and ensuing high pill burden, and cost of goods.

There is a need for HCV inhibitors that may overcome the disadvantages of current HCV therapy such as side effects, limited efficacy, the emerging of resistance, and compliance failures, as well as improve the sustained viral response.

The present invention concerns a group of HCV-inhibiting 1-(8-hydroxy-7-(hydroxymethyl)-1,6-dioxaspiro[3.4]octan-5-yl)pyrimidine-2,4-dione derivatives with useful properties regarding one or more of the following parameters: antiviral efficacy, favorable profile of resistance development, lack of toxicity and genotoxicity, favorable pharmacokinetics and pharmacodynamics and ease of formulation and administration. Spirooxetane nucleosides, in particular 1-(2-O,2-C-ethano-β-D-ribofuranosyl)thymine and 1-(2-O,2-C-ethano-β-D-ribofuranosyl)uracil have been described in Org. Biomol. Chem., 2003, 3514-3526. These compounds were tested against HIV, but no activity was found.

Compounds of the invention may also be attractive due to the fact that they lack activity against other viruses, in particular against HIV. HIV-infected patients often suffer from co-infections such as HCV. Treatment of such patients with an HCV inhibitor that also inhibits HIV may lead to the emergence of resistant HIV strains.

DESCRIPTION OF THE INVENTION

In one aspect the present invention provides compounds that can be represented by the formula I:

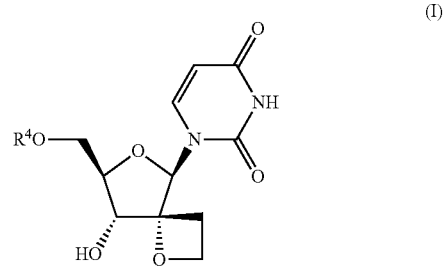

including any possible stereoisomers thereof, wherein:
$R^4$ is a monophosphate, diphosphate or triphosphate ester; or
$R^4$ is a group of formula

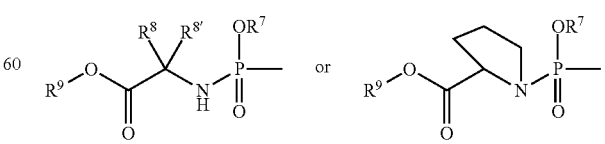

$R^7$ is phenyl, optionally substituted with 1, 2, or with 3 substituents each independently selected from halo, $C_1$-$C_6$alkyl, $C_3$-$C_6$alkenyl, $C_1$-$C_6$alkoxy, hydroxy, and amino; or R⁷ is naphthyl, optionally substituted with 1, 2, or with 3 substituents each independently selected from halo, C₁-C₆alkyl, C₃-C₆alkenyl, C₁-C₆alkoxy, hydroxy, and amino; or R⁷ is indolyl, optionally substituted with one C₁-C₆alkyloxycarbonyl group and optionally further with 1, 2, or with 3 substituents each independently selected from halo, C₁-C₆alkyl, C₃-C₆alkenyl, C₁-C₆alkoxy, hydroxy, and amino;

R⁸ is hydrogen, C₁-C₆alkyl, benzyl, or phenyl;
R⁸' is hydrogen, C₁-C₆alkyl, benzyl, or phenyl; or
R⁸ and R⁸' together with the carbon atom to which they are attached form C₃-C₇cycloalkyl;
R⁹ is C₁-C₁₀alkyl, C₃-C₇cycloalkyl, phenyl or phenyl-C₁-C₆alkyl, wherein the phenyl moiety in phenyl or phenyl-C₁-C₆alkyl is optionally substituted with 1, 2 or 3 substituents each independently selected from hydroxy, C₁-C₆alkoxy, amino, mono- and diC₁-C₆alkylamino;
or the pharmaceutically acceptable salts or solvates thereof.

In a further aspect, the invention concerns the use of compounds of formula I, as specified herein, for inhibiting HCV. Alternatively, there is provided the use for the manufacture of a medicament of a compound of formula I, as specified herein; for inhibiting HCV.

The group —NH—C(R⁸)(R⁸')—C(=O)— may form an amino acid residue, which includes natural and non-natural amino acid residues. Of interest are glycine (Gly) and dimethyl glycine (Dmg). Also of interest are those amino acid residues wherein R⁸' is hydrogen. Where in the latter instance R⁸ is other than hydrogen, the amino acid residue has a chiral center and the configuration at the asymmetric carbon atom may be that of an L-amino acid. Examples include alanine (Ala), valine (Val), isoleucine (Ile), α-aminobutyric acid (ABA also named 2-aminobutyric acid or ethylglycine), phenylalanine (Phe) and phenylglycine (Phg) residues, in particular L-Ala, L-Val, L-Ile, L-ABA, L-Phe and L-Phg. An example of an amino acid residue wherein R⁸ and R⁸' together with the carbon atom to which they are attached form C₃-C₇cycloalkyl, is 1,1-cyclopropylamino acid. Similarly, the group

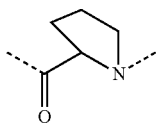

forms a proline residue, preferably an L-proline residue.

Subgroups of compounds of formula I are those compounds of formula I, or subgroups of compounds of formula I, as defined herein, wherein R⁴ is a group of formula

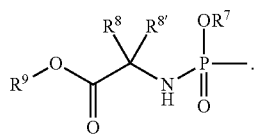

Subgroups of compounds of formula I are those compounds of formula I, or subgroups of compounds of formula I, as defined herein, wherein:
(a) R⁷ is phenyl, optionally substituted with 1, 2, or with 3 substituents each independently selected from halo, C₁-C₆alkyl, C₃-C₆alkenyl, C₁-C₆alkoxy, hydroxy, and amino; or R⁷ is naphthyl, optionally substituted with halo, C₁-C₆alkyl, or C₁-C₆alkoxy; or R⁷ is indolyl;
(b) R⁷ is phenyl, optionally substituted with 1, with 2, or with 3 substituents each independently selected from halo, C₁-C₆alkyl, C₃-C₆alkenyl, C₁-C₆alkoxy, hydroxy, and amino; or R⁷ is naphthyl; or R⁷ is indolyl;
(c) R⁷ is phenyl, optionally substituted with 1 or with 2 substituents each independently selected from halo, C₁-C₆alkyl, C₃-C₆alkenyl, C₁-C₆alkoxy, hydroxy, and amino; or R⁷ is naphthyl; or R⁷ is indolyl;
(d) R⁷ is phenyl, optionally substituted with 1 or with 2 substituents each independently selected from halo, C₁-C₆alkyl, C₃-C₆alkenyl, and C₁-C₆alkoxy, or R⁷ is naphthyl;
(e) R⁷ is phenyl, optionally substituted with halo or with 1 or 2 C₁-C₆alkyl radicals, or R⁷ is naphthyl;
(f) R⁷ is phenyl, halophenyl, diC₁-C₄alkylphenyl, or naphthyl;
(g) R⁷ is phenyl;
(h) R⁷ is naphthyl;
(i) R⁷ is 5-indolyl.

In one embodiment R⁷ is indolyl, optionally substituted at its nitrogen atom with one C₁-C₆alkyloxy-carbonyl group and optionally at its carbon atoms with further with 1, 2, or with 3 substituents each independently selected from halo, C₁-C₆alkyl, C₃-C₆alkenyl, C₁-C₆alkoxy, hydroxy, and amino;

In a further embodiment, the group R⁷ being indolyl in the compounds of formula I or any of the subgroups thereof, is 5-indolyl or the group R⁷ being N—C₁-C₆alkyloxy-carbonylindolyl is N-t.butyloxycarbonyl-5-indolyl, in particular N-t.butyloxycarbonyl-5-indolyl. The indolyl group when linked at its 5-position may be represented as follows:

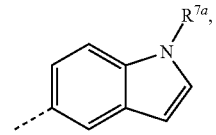

wherein R⁷ᵃ is hydrogen or C₁-C₆alkyloxy-carbonyl, or in particular R⁷ᵃ is hydrogen, C₁-C₄alkyloxycarbonyl, or more in particular R⁷ᵃ is hydrogen or t.butyloxycarbonyl. In a further embodiment, the group indolyl in the compounds of formula I or any of the subgroups thereof is 5-indolyl (i.e. wherein R⁷ᵃ is hydrogen).

Subgroups of compounds of formula I are those compounds of formula I, or subgroups of compounds of formula I, as defined herein, wherein
(a) R⁸ is methyl and R⁸' is methyl; or
(b) R⁸ is hydrogen and R⁸' is phenyl, C₁-C₆alkyl or C₁-C₄alkyl, such as methyl, ethyl, isopropyl or isobutyl.

Subgroups of compounds of formula I are those compounds of formula I, or subgroups of compounds of formula I, as defined herein, wherein the

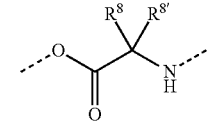

moiety is glycyl, dimethylglycyl, α-aminobutyryl, phenylglycine, isoleucyl, alanyl, phenylalanyl or valyl (respectively Gly, Dmg, ABA, Phg, Ile, Ala, Phe or Val; in particular L-ABA, L-Phg, L-Ile, L-Ala, L-Phe or L-Val).

Subgroups of compounds of formula I are those compounds of formula I, or of subgroups of compounds of formula I, as defined herein, wherein $R^8$ is hydrogen, $C_1$-$C_6$alkyl, benzyl, or phenyl; and $R^{8'}$ is hydrogen, $C_1$-$C_6$alkyl, benzyl, or phenyl.

Subgroups of compounds of formula I are those compounds of formula I, or subgroups of compounds of formula I, as defined herein, wherein the

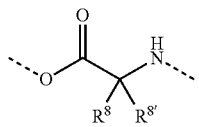

moiety has the structure

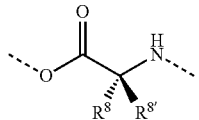

wherein $R^8$ is hydrogen and $R^{8'}$ is hydrogen, phenyl, $C_1$-$C_6$alkyl, benzyl; or $R^8$ is hydrogen and $R^{8'}$ is hydrogen or $C_1$-$C_6$alkyl;

$R^8$ is hydrogen and $R^{8'}$ is $C_1$-$C_2$alkyl;

$R^8$ is hydrogen and $R^{8'}$ is methyl.

In one embodiment $R^8$ and $R^{8'}$ together with the carbon atom to which they are attached form $C_3$-$C_7$cycloalkyl; or in particular form $C_3$-$C_4$cycloalkyl; or in particular form cyclopropyl.

Subgroups of compounds of formula I are those compounds of formula I, or of subgroups of compounds of formula I, as defined herein, wherein (a) $R^9$ is $C_1$-$C_6$alkyl, benzyl, or phenyl optionally substituted with 1, 2 or 3 substituents each independently selected from hydroxy, $C_1$-$C_6$alkoxy, amino, mono- and di$C_1$-$C_6$alkylamino;

(b) $R^9$ is $C_1$-$C_6$alkyl or benzyl;

(c) $R^9$ is $C_1$-$C_6$alkyl;

(d) $R^9$ is $C_1$-$C_4$alkyl;

(e) $R^9$ is methyl, ethyl, or t-butyl;

(f) $R^9$ is $C_3$-$C_7$cycloalkyl.

Of interest are compounds 12a, 12b, 12c, 12d, 12e, 12f, 12g, 12h, 12i, 12j, 12k, 12l, 12m mentioned in the section "Examples" as well as the pharmaceutically acceptable acid addition salts of these compounds. Of particular interest are compounds 12a, 12c, 12d and 12k, either in the free-form (i.e. non-salt form) of these compounds or as a pharmaceutically acceptable acid addition salt thereof.

The compounds of formula I have several centers of chirality, in particular at the carbon atoms 1', 3', and 4'. Although the stereochemistry at these carbon atoms is fixed, the compounds may display at least 75%, preferably at least 90%, such as in excess of 95%, or of 98%, enantiomeric purity at each of the chiral centers.

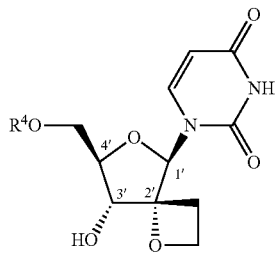

Chirality may also be present in the substituents, such as where $R^4$ is

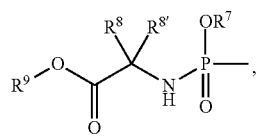

which can have chirality at the $R^8$ bearing carbon (where $R^8$ and $R^{8'}$ are different) and at the phosphorus atom. The phosphorus center can be present as $R_P$ or $S_P$, or a mixture of such stereoisomers, including racemates. Diastereoisomers resulting from the chiral phosphorus center and a chiral carbon atom may exist as well.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b.

The compounds of formula I are represented as a defined stereoisomer, except for the stereoisomerism at the phosphorous atom of the phosphoramidate group. The absolute configuration of such compounds can be determined using art-known methods such as, for example, X-ray diffraction or NMR and/or implication from starting materials of known stereochemistry. Pharmaceutical compositions in accordance with the invention will preferably comprise stereoisomerically pure forms of the indicated stereoisomer of the particular compound of formula I.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%, or of 98% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary layers. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography.

The pharmaceutically acceptable addition salts comprise the therapeutically active non-toxic acid and base addition salt forms of the compounds of formula I. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula I containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in their tautomeric form. For example, tautomeric forms of amide (—C(=O)—NH—) groups are iminoalcohols (—C(OH)=N—), which can become stabilized in rings with aromatic character. The uridine base is an example of such a form. Such forms, although not explicitly indicated in the structural formulae represented herein, are intended to be included within the scope of the present invention.

As used herein "$C_1$-$C_4$alkyl" as a group or part of a group defines saturated straight or branched chain hydrocarbon radicals having from 1 to 4 carbon atoms such as for example methyl, ethyl, 1-propyl, 2-propyl, 1-butyl, 2-butyl, 2-methyl-1-propyl, 2-methyl-2-propyl. "$C_1$-$C_6$alkyl" encompasses $C_1$-$C_4$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl. "$C_1$-$C_{10}$alkyl" encompasses $C_1$-$C_6$alkyl radicals and the higher homologues thereof having 7, 8, 9 or 10 carbon atoms such as, for example, heptyl, 2-heptyl, 3-heptyl, 2-methylhexyl, octyl, 2-octyl, 3-octyl, nonyl, 2-nonyl, 3-nonyl, 2-butylpentyl, decyl, 2-decyl, and the like. Of interest amongst $C_1$-$C_{10}$alkyl is $C_1$-$C_6$alkyl, $C_1$-$C_2$alkyl defines methyl and ethyl.

'$C_1$-$C_6$alkoxy' means a radical —O—$C_1$-$C_6$alkyl wherein $C_1$-$C_6$alkyl is as defined above. Examples of $C_1$-$C_6$alkoxy are methoxy, ethoxy, n-propoxy, or isopropoxy.

"$C_3$-$C_6$cycloalkyl" includes cyclopropyl, cyclobutyl, cyclopentyl and cyclohexyl. Of interest is cyclopropyl.

The term "$C_3$-$C_6$alkenyl" as a group or part of a group defines straight and branched chained hydrocarbon radicals having saturated carbon-carbon bonds and at least one double bond, and having from 3 to 6 carbon atoms, such as, for example, 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_3$-$C_6$alkenyl is $C_3$-$C_4$alkenyl. Of interest amongst $C_3$-$C_6$alkenyl or $C_3$-$C_4$alkenyl are those radicals having one double bond.

The term 'halo' is generic to fluoro, chloro, bromo and iodo.

In one embodiment, the term "phenyl-$C_1$-$C_6$alkyl" is benzyl.

As used herein, the term '(=O)' or 'oxo' forms a carbonyl moiety when attached to a carbon atom. It should be noted that an atom can only be substituted with an oxo group when the valency of that atom so permits.

The term "monophosphate, diphosphate or triphosphate ester" refers to groups:

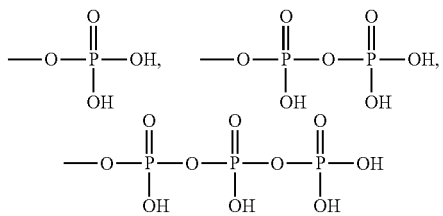

Where the position of a radical on a molecular moiety is not specified (for example a substituent on phenyl) or is represented by a floating bonds, such radical may be positioned on any atom of such a moiety, as long as the resulting structure is chemically stable. When any variable is present more than once in the molecule, each definition is independent.

Whenever used herein, the term 'compounds of formula I', or 'the present compounds' or similar terms, it is meant to include the compounds of formula I, including the possible stereochemically isomeric forms, and their pharmaceutically acceptable salts and solvates.

The present invention also includes isotope-labeled compounds of formula I or any subgroup of formula I, wherein one or more of the atoms is replaced by an isotope that differs from the one(s) typically found in nature. Examples of such isotopes include isotopes of hydrogen, such as $^2$H and $^3$H;

carbon, such as $^{11}$C, $^{13}$C and $^{14}$C; nitrogen, such as $^{13}$N and $^{15}$N; oxygen, such as $^{15}$O, [17]O and $^{18}$O; phosphorus, such as $^{31}$P and $^{32}$P, sulphur, such as $^{35}$S; fluorine, such as $^{18}$F; chlorine, such as [36]Cl; bromine such as [75]Br, [76]Br, [77]Br and [82]Br; and iodine, such as $^{123}$I, [124]I, $^{125}$I and [131]I. Isotope-labeled compounds of the invention can be prepared by processes analogous to those described herein by using the appropriate isotope-labeled reagents or starting materials, or by art-known techniques. The choice of the isotope included in an isotope-labeled compound depends on the specific application of that compound. For example, for tissue distribution assays, a radioactive isotope such as $^3$H or $^{14}$C is incorporated. For radio-imaging, imaging applications, a positron emitting isotope such as $^{11}$C, $^{18}$F, $^{13}$N or $^{15}$O will be useful. The incorporation of deuterium may provide greater metabolic stability, resulting in, e.g. an increased in vivo half life of the compound or reduced dosage requirements.

Synthesis Procedures

The starting material 1-[(4R,5R,7R,8R)-8-hydroxy-7-(hydroxymethyl)-1,6-dioxaspiro[3.4]octan-5-yl]pyrimidine-2,4 (1H,3H)-dione 10 can be prepared as follows. Intermediate 4 can be obtained as described in Org. Lett., 2007, 9, 3009-3012 and is reacted with allylmagnesium bromide to intermediate 5. The hydroxy group in the latter is benzoylated with benzoyl chloride in the presence of a base, for example a trialkylamine such as triethylamine, or N,N-dimethylpyridin-4-amine (DMAP), resulting in intermediate 6. The latter intermediate is activated with a Lewis acid, in particular with SnCl$_4$, and reacted with a silylated uracil, obtained for example by reacting uracil with N,O-bis[Trimethylsilyl]acetamide (BSA). This reaction yields intermediate 7 in which the double bond in the allyl group is oxidized with osmium tetroxide in the presence of periodate to an aldehyde, which is subsequently reduced to the corresponding alcohol 8. Mesylation of the latter with mesyl chloride in the presence of a base, for example pyridine, followed by treatment with a strong base such as sodium hydride results in oxetane formation. Removal of the benzyl groups in 9, e.g. with hydrogen in the presence of a noble metal catalyst, e.g. palladium hydroxide, yields intermediate 10. The latter can be reacted with a phosphoramidochloridic acid ester 11a or 11b in the presence of a base, e.g. N-methylimidazole (NMI).

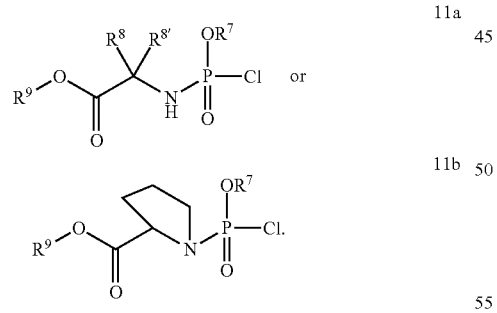

The above described reactions are illustrated in the following scheme.

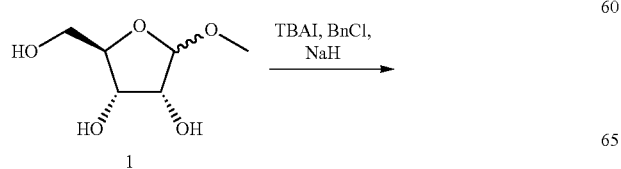

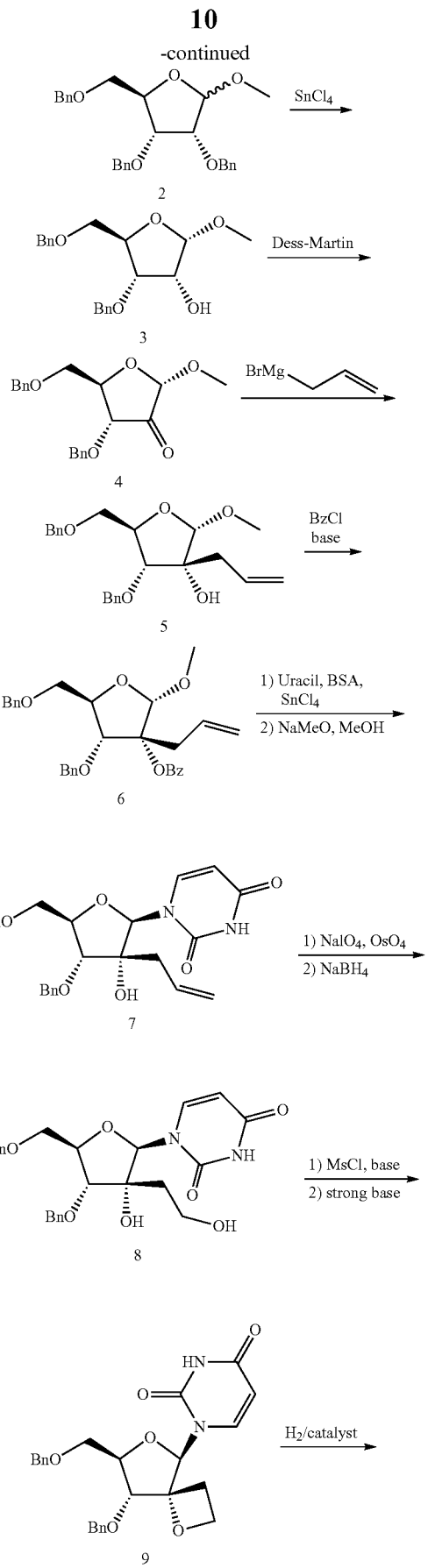

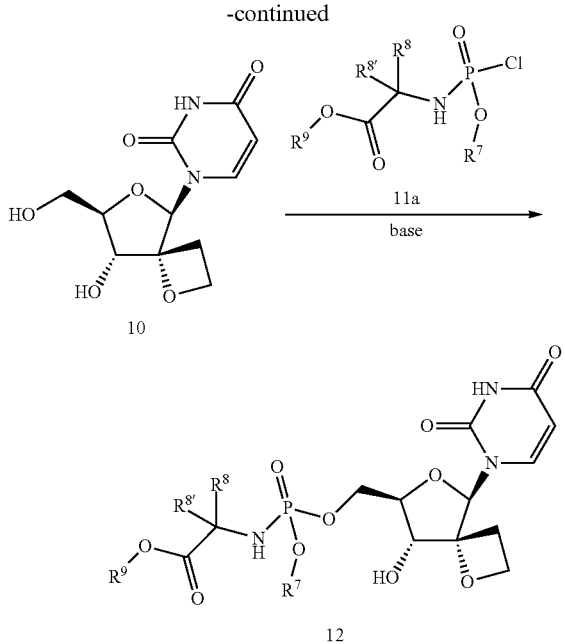

The phosphoramidochloridic acid ester 11a or 11b can be prepared by reacting an alcohol 1a with POCl₃ in the presence of a base, thus obtaining phosphoryl dichloride 1b, which is further reacted with the amino acid 1c or 1d.

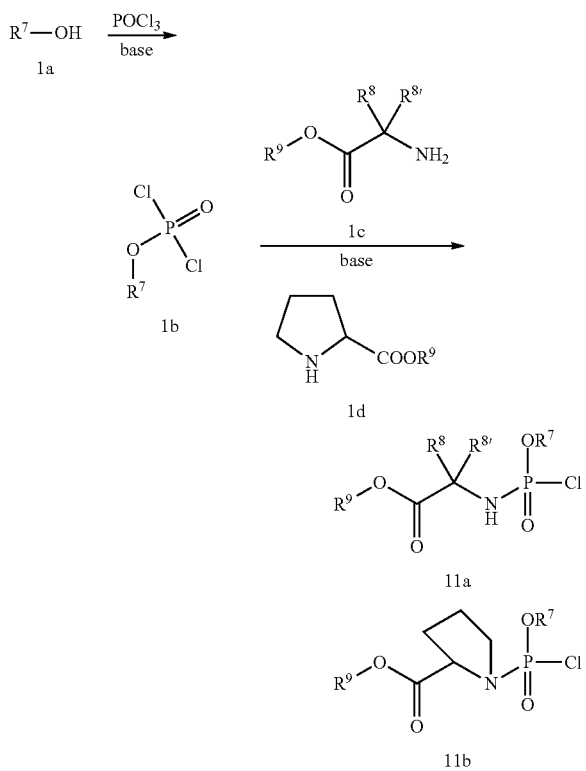

In a further aspect, the present invention concerns a pharmaceutical composition comprising a therapeutically effective amount of a compound of formula I as specified herein, and a pharmaceutically acceptable carrier. Said composition may contain from 1% to 50%, or from 10% to 40% of a compound of formula I and the remainder of the composition is the said carrier. A therapeutically effective amount in this context is an amount sufficient to act in a prophylactic way against HCV infection, to inhibit HCV, to stabilize or to reduce HCV infection, in infected subjects or subjects being at risk of becoming infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

The compounds of formula I or of any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and HCC. A number of the compounds of this invention moreover are believed to be active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavorable phenomena such as insufficient quick onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their anti-HCV properties, the compounds of formula I, including any possible stereoisomers, the pharmaceutically acceptable addition salts or solvates thereof, are useful in the treatment of warm-blooded animals, in particular humans, infected with HCV, and in the prophylaxis of HCV infections. The compounds of the present invention may therefore be used as a medicine, in particular as an anti-HCV or a HCV-inhibiting medicine. The present invention also relates to the use of the present compounds in the manufacture of a medicament for the treatment or the prevention of HCV infection. In a further aspect, the present invention relates to a method of treating a warm-blooded animal, in particular human, infected by HCV, or being at risk of becoming infected by HCV, said method comprising the administration of an anti-HCV effective amount of a compound of formula I, as specified herein. Said use as a medicine or method of treatment comprises the systemic administration to HCV-infected subjects or to subjects susceptible to HCV infection of an amount effective to combat the conditions associated with HCV infection.

In general it is contemplated that an antiviral effective daily amount would be from about 1 to about 200 mg/kg, or about 5 to about 175 mg/kg, or about 10 to about 150 mg/kg, or about 20 to about 100 mg/kg, or about 50 to about 75 mg/kg body weight. Average daily doses can be obtained by multiplying these daily amounts by about 70. It may be appropriate to administer the required dose as two, three, four or more sub-doses at appropriate intervals throughout the day. Said sub-doses may be formulated as unit dosage forms, for example, containing about 1 to about 5000 mg, or about 50 to about 3000 mg, or about 100 to about 1000 mg, or about 200 to about 600 mg, or about 100 to about 400 mg of active ingredient per unit dosage form.

As used herein the term "about" has the meaning known to the person skilled in the art. In certain embodiments the term "about" may be left out and the exact amount is meant. In other embodiments the term "about" means that the numerical following the term "about" is in the range of ±15%, or of ±10%, or of ±5%, or of ±1%, of said numerical value.

EXAMPLES

The following schemes are just meant to be illustrative and are by no means limiting the scope.

LC-MS analysis was done using either one of the following methods. NMR data were recorded on a Bruker 400 MHz spectrometer.

HPLC Condition A
System: Waters Alliance 2695
Column: Waters XTerra 2.5 μm 4.6×50 mm; Column temp.: 55° C.; Flow: 2 mL/min
Mobile phase A: 10 mM ammonium acetate+0.1% HCOOH in $H_2O$
Mobile phase B: $CH_3CN$

| Time | % A | % B |
| --- | --- | --- |
| 0.00 | 85 | 15 |
| 3.00 | 5 | 95 |
| 4.20 | 5 | 95 |
| 4.30 | 85 | 15 |
| 5.40 | 85 | 15 |

HPLC Condition B
System: Waters Alliance 2695
Column: Hypercarb 3μ 4.6×50 mm; Column temp.: 50° C.; Flow: 2 mL/min
Mobile phase A: 10 mM ammonium acetate in $H_2O/CH_3CN$ 1/9
Mobile phase B: 10 mM ammonium acetate in $H_2O/CH_3CN$ 9/1

| Time | % A | % B |
| --- | --- | --- |
| 0.00 | 0 | 100 |
| 3.00 | 100 | 0 |
| 4.20 | 100 | 0 |
| 4.30 | 0 | 100 |
| 5.40 | 0 | 100 |

Example 1

(2S,3R,4R,5R)-3-allyl-4-(benzyloxy)-5-(benzyloxymethyl)-2-methoxytetrahydrofuran-3-ol (5)

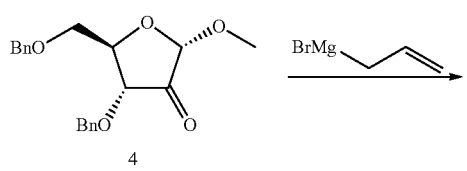

-continued

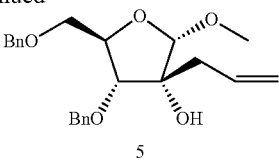
5

Under argon atmosphere, to a solution of 4 (obtained as in Org. Lett., 2007, 9, 3009-3012) in dry tetrahydrofurane (THF; 400 mL) at −78° C., allylmagnesium bromide (400 mL, 400 mmol; 1.0 M in diethylether) was added. After stirring the reaction mixture at −78° C. for 4 hours, the reaction mixture was allowed to stir at room temperature for 2 hours. The reaction was carefully quenched with saturated aqueous ammonium chloride. The mixture was extracted with dichloromethane, and the organic layer was washed with brine. The solvent was removed, and the residue was purified by silica gel chromatography (600 g silica), by gradient elution with 15% to 20% ethyl acetate in hexane to give the reaction product 5 as a colorless oil (32.9 g, 70%). HPLC Condition A, Rt: 2.97 min, m/z=402 (M+NH$_4$)$^+$. $^1$H NMR (400 MHz, CDCl$_3$) δ ppm 7.38-7.20 (m, 10H), 5.84-5.97 (m, 1H), 5.12 (d, 1H, J=10.2 Hz), 5.01 (d, 1H, J=17.2 Hz), 4.74 (d, 1H, J=12.3 Hz), 4.56 (s, 1H), 4.53-4.40 (m, 3H), 4.05-4.11 (m, 1H), 3.32-3.53 (m, 4H), 3.44 (s, 3H), 2.37 (dd, 1H, J=14.3, 6.7 Hz), 2.25 (dd, 1H, J=14.3, 7.6 Hz).

Example 2

(2S,3R,4R,5R)-3-allyl-4-(benzyloxy)-5-(benzyloxymethyl)-2-methoxytetrahydrofuran-3-ylbenzoate (6)

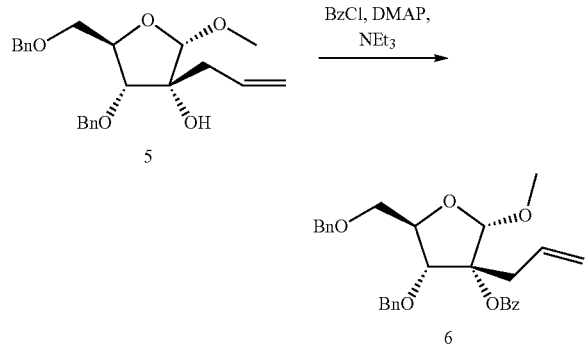

To a solution of 5 (26.6 g, 69.2 mmol) in dry dichloromethane (500 mL) at room temperature, N,N-dimethylpyridin-4-amine (DMAP; 2.113 g, 17.30 mmol), triethylamine (217 mL, 1557 mmol) and benzoyl chloride (18.05 mL, 156 mmol) were added. After 1 hour, additional benzoyl chloride (6 mL) and DMAP (2.1 g) were added. The mixture was stirred for 5 days.

The reaction mixture was then stirred with 1 N HCl and extracted with dichloromethane. The organic layers were combined and washed with saturated aqueous NaHCO$_3$ followed by brine. After drying with MgSO$_4$, filtration and evaporation of the volatiles, the residue was purified by column chromatography (400 g silica) eluting with heptane to 15% ethyl acetate in heptane to give reaction product as an oil (as a mixture with compound 5). The mixture was purified again with CH$_2$Cl$_2$ as eluent (400 g silica). The pure fractions were collected and intermediate 6 was obtained as a colorless oil (13.05 g, 39%). HPLC Condition A, Rt: 3.41 min, m/z=457 (M-OMe)$^+$. $^1$H NMR (400 MHz, CDCl$_3$) δ ppm 8.1 (d, 2H, J=7.9 Hz), 7.68-7.28 (m, 13H), 5.84-5.77 (m, 1H), 5.12 (d, 1H, J=16 Hz), 4.95 (d, 1H, J=16 Hz), 4.92 (d, 1H, J=12.3 Hz), 4.56 (d, 1H, J=12.3 Hz), 4.48 (d, 1H, J=11.6 Hz), 4.40 (d, 1H, J=11.6 Hz), 4.2 (m, 1H), 3.85 (d, 1H, J=6.2 Hz), 3.53 (d, 1H, J=10.8 Hz), 3.7 (s, 3H), 3.45 (dd, 1H, J=10.8, 6.2 Hz), 3.25 (dd, 1H, J=15.5, 7.3 Hz), 2.45 (dd, 1H, J=15.5, 7.3 Hz).

Example 3

1-[(2R,3R,4R,5R)-3-allyl-4-(benzyloxy)-5-(benzyloxymethyl)-3-hydroxytetrahydrofuran-2-yl]pyrimidine-2,4(1H,3H)-dione (7)

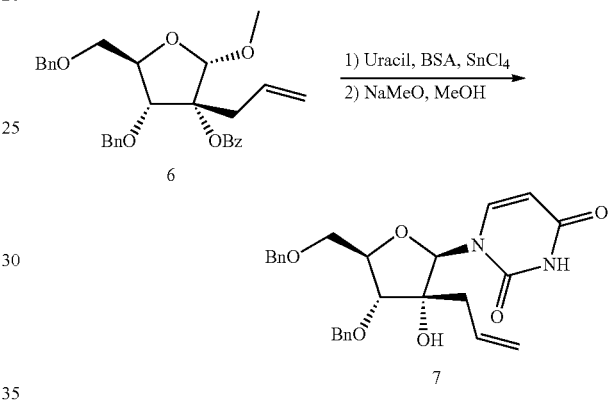

Bis(trimethylsilyl)acetamide (BSA; 29.2 mL, 118 mmol) was added to a mixture of 6 (14.0 g, 23.1 mmol) and uracil (5.99 g, 53.4 mmol) in anhydrous acetonitrile (300 mL). The reaction mixture was refluxed for 1 hour and the clear solution was allowed to cool down to room temperature. Tinchloride (11.55 mL, 99 mmol) was added dropwise at room temperature and the mixture was further stirred for 1 hour. The mixture was then stirred at reflux for 1.5 hour and again cooled to room temperature. Ethyl acetate (250 mL) was added, followed by saturated aqueous NaHCO$_3$ (250 mL) and the mixture was stirred for 15 minutes. After filtration through Celite, the organic layer was separated and washed with saturated aqueous NaHCO$_3$ (250 mL). The combined aqueous layer was extracted with ethyl acetate (250 mL) and the combined organic layer was dried (MgSO$_4$), filtered and evaporated to dryness under reduced pressure. The resulting yellow oil was dissolved in methanol and 25% sodium methanolate (25 mL) was added. Stirring continued overnight. More 25% sodium methanolate (15 mL) was added and stirring was continued overnight. Acetic acid (30 mL) was added and the solvent was removed. The residue was purified by column chromatography with heptane/ethyl acetate 50:50 to 100% ethyl acetate. Intermediate 7 (9.38 g, 76%) was obtained as a colorless oil. HPLC Condition A, Rt: 2.49 min, m/z=465 (M+H)$^+$. $^1$H NMR (400 MHz, CDCl$_3$) δ ppm 8.39 (1H, NH), 7.75 (d, 1H, J=8.0 Hz), 7.22-7.43 (m, 10H), 6.05 (s, 1H), 5.71-5.84 (m, 1H), 5.35 (d, 1H, J=8.0 Hz), 5.00-5.11 (m, 2H), 4.70 (d, 1H, J=11.5 Hz), 4.53 (d, 1H, J=11.5 Hz), 4.47 (d, 1H, J=11.1 Hz), 4.47 (d, 1H, J=11.1 Hz), 4.11-4.16 (m, 1H), 4.04 (d, 1H, J=8.0 Hz), 3.81-3.87 (m, 1H), 3.45-3.52 (m, 1H), 3.17 (bs, OH), 2.15-2.33 (m, 2H).

Example 4

1-[(2R,3R,4R,5R)-4-(benzyloxy)-5-(benzyloxymethyl)-3-hydroxy-3-(2-hydroxyethyl)tetrahydrofuran-2-yl]pyrimidine-2,4(1H,3H)-dione (8)

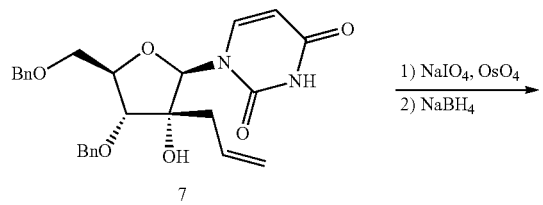

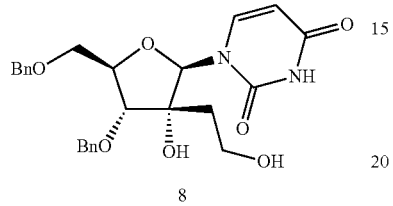

To a stirred solution of 7 (7.8 g, 16.79 mmol) in a mixture of THF (10 mL) and H$_2$O (10 mL) was added sodium periodate (11.17 g, 52.2 mmol) followed by osmium(VIII) tetroxide (2 mL, 2.5 w/v % in tert-Butanol, 0.168 mmol) and stirring was continued for 2 hour at room temperature. Water (100 mL) was added and extraction was performed with ethyl acetate (2×50 mL). The organic layer was washed with saturated aqueous NaHCO$_3$ (2×30 mL). The combined aqueous layer was extracted with ethyl acetate and the combined organic layer was dried over (Na$_2$SO$_4$), filtered and evaporated to dryness under reduced pressure. The oily residue obtained was dissolved in a mixture of THF (100 mL) and H$_2$O (20 mL) and sodium borohydride (1.361 g, 36.0 mmol) was added. The reaction mixture was stirred overnight at room temperature, whereupon water (100 mL) was added and extraction was performed with ethyl acetate (2×50 mL). The combined organic layer was washed with saturated aqueous NaHCO$_3$, the combined aqueous layer was extracted with ethyl acetate, and the combined organic layer was dried over (Na$_2$SO$_4$), filtered and evaporated to dryness under reduced pressure. The oily residue obtained was purified by column chromatography (0-10% (v/v) methanol in CH$_2$Cl$_2$ then 10% isocratic) affording reaction product 8 as a white foam (4.8 g, 57%). HPLC Condition A, Rt: 2.12 min, m/z=469 (M+H)$^+$. $^1$H NMR (400 MHz, CDCl$_3$) δ ppm 9.85 (1H, NH), 7.85 (d, 1H, J=8.0 Hz), 7.22-7.43 (m, 10H), 6.05 (s, 1H), 5.35 (d, 1H, J=8.0 Hz), 4.75 (d, 1H, J=11.5 Hz), 4.53 (d, 1H, J=11.5 Hz), 4.45 (d, 1H, J=11.3 Hz), 4.35 (d, 1H, J=11.3 Hz), 4.27 (d, 1H, J=6.6 Hz), 4.2 (s, 1H), 4.1, (d, 1H, J=6.6 Hz), 3.95 (d, 1H, J=10.8 Hz), 3.75-3.7 (m, 1H), 3.62 (d, 1H, J=10.8 Hz), 3.17 (bs, OH), 1.8-1.7 (m, 2H).

Example 5

1-[(4R,5R,7R,8R)-8-(benzyloxy)-7-(benzyloxymethyl)-1,6-dioxaspiro[3.4]octan-5-yl]pyrimidine-2,4(1H,3H)-dione (9)

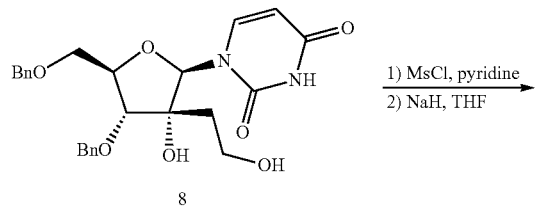

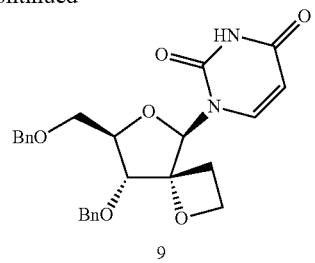

Methanesulfonyl chloride (0.800 mL, 10.34 mmol) was added to 8 (4.32 g, 9.22 mmol) in dry pyridine (100 mL). After 1 hour and 15 minutes, 0.1 equivalents more methanesulfonyl chloride was added and the mixture was further stirred at room temperature for 45 minutes. Then, a small amount of methanol was added and the mixture was evaporated to dryness. The residue was dissolved in ethyl acetate (100 mL) and washed with saturated NaHCO$_3$ (2×50 mL). The combined aqueous layer was extracted with ethyl acetate. The combined organic layer was then dried over Na$_2$SO$_4$ and concentrated in vacuo. The obtained residue was dissolved in dry THF and 95% NaH (932 mg, 36.9 mmol) was added at once at room temperature. After stirring for 2 hours at room temperature, the reaction mixture was poured on a saturated aqueous solution of NH$_4$Cl (30 mL) followed by addition of CH$_2$Cl$_2$ (250 mL). The separated organic layer was washed with saturated aqueous NaHCO$_3$ (2×100 mL) and the combined aqueous layer was extracted with CH$_2$Cl$_2$ (250 mL). The combined organic layer was dried (Na$_2$SO$_4$), filtered and evaporated to dryness under reduced pressure. The residue obtained was purified by column chromatography eluting first with heptane, then with ethyl acetate to afford 9 (3.27 g, 79%) as a foam. HPLC Condition A, Rt: 2.33 min, m/z=451 (M+H)$^+$. $^1$H NMR (400 MHz, CDCl$_3$) δ ppm 2.20-2.38 (m, 1H) 2.38-2.52 (m, 1H) 3.62-3.73 (m, 1H) 3.89-4.13 (m, 3H) 4.38-4.56 (m, 3H) 4.56-4.68 (m, 1H) 4.70-4.88 (m, 2H) 5.25 (d, J=8.00 Hz, 1H) 6.25 (s, 1H) 7.18-7.47 (m, 10H) 7.87 (d, J=8.20 Hz, 1H) 8.90 (br. s., 1H)

Example 6

1-[(4R,5R,7R,8R)-8-hydroxy-7-(hydroxymethyl)-1,6-dioxaspiro[3.4]octan-5-yl]pyrimidine-2,4(1H,3H)-dione (10)

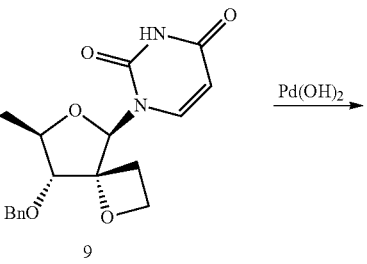

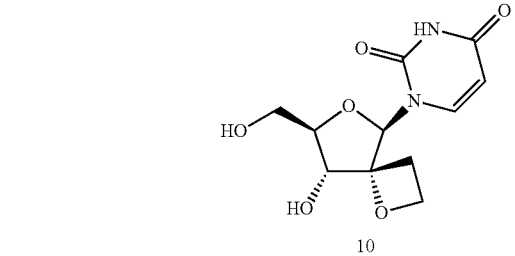

A mixture of 9 (50 mg, 0.111 mmol) in methanol (1 mL) and Pd(OH)$_2$ (8 mg) was stirred under a hydrogen atmosphere at room temperature. After 4 hours, more Pd(OH)$_2$ (30 mg) and methanol (1 mL) were added. The mixture was stirred vigorously under H$_2$-atmosphere overnight. The catalyst was removed by filtration over decalite, and the solvent was removed by evaporation. The resulting residue was purified by silica gel chromatography eluted with 10% methanol in ethyl acetate to give the intermediate 10 as white powder (16.8 mg; 56%). HPLC Condition B, Rt: 1.98 min, m/z=271 (M+H)$^+$. $^1$H NMR (400 MHz, D$_2$O) δ ppm 7.65 (d, 1H, J=8.0 Hz), 6.11 (s, 1H), 5.82 (d, 1H, J=8.0 Hz), 4.46-4.61 (m, 2H), 4.06-4.13 (m, 1H), 3.87-3.95 (m, 1H), 3.69-3.77 (m, 2H), 2.62-2.73 (m, 1H), 2.48-2.58 (m, 1H).

Example 7 methyl 2-(chloro(phenoxy)phosphorylamino)-2-methylpropionate (11)

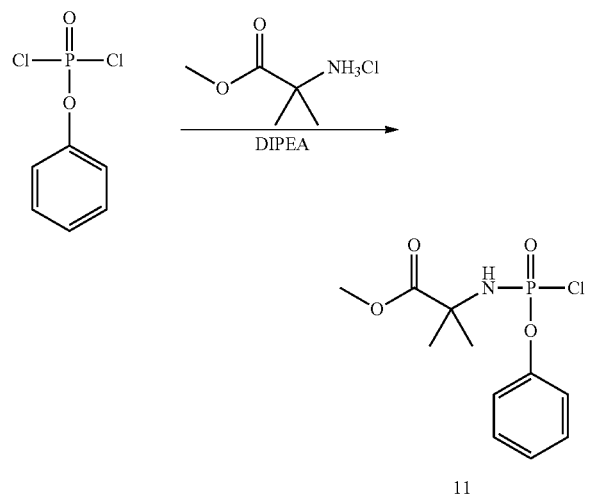

A solution of phenylphosphorodichloridate (1.0 eq., 13.0 mmol, 1.9 mL) and methyl α-aminoisobutyrate hydrochloride (1.0 eq., 13.0 mmol, 2.0 g) in CH$_2$Cl$_2$ (80 mL) was cooled to −80° C. Dry N,N-diisopropylethylamine (DIPEA; 2.0 eq., 26.0 mmol, 4.3 mL) was added dropwise. After 2 hours, the reaction was warmed to room temperature and the solvent was removed under reduced pressure. Dry diethylether was added and the precipitate was filtered off and washed twice with dry diethylether under an argon atmosphere. The filtrate was evaporated to dryness to give 11 which was stored as a 0.90 M solution in dry tetrahydrofuran (THF) at −18° C.

Example 8 methyl 2-[[[(4R,5R,7R,8R)-5-(2,4-dioxo-3,4-dihydropyrimidin-1(2H)-yl)-8-hydroxy-1,6-dioxaspiro [3.4]octan-7-yl]methoxy](phenoxy)phosphorylamino]-2-methylpropanoate (12e)

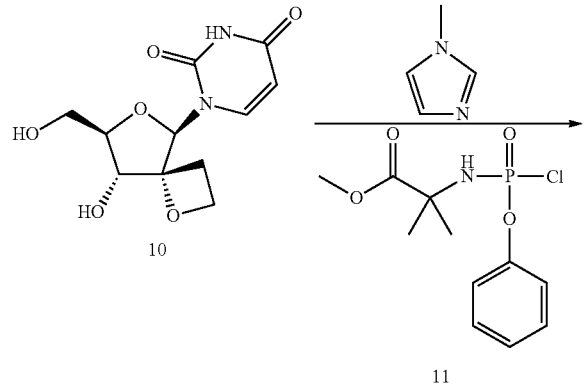

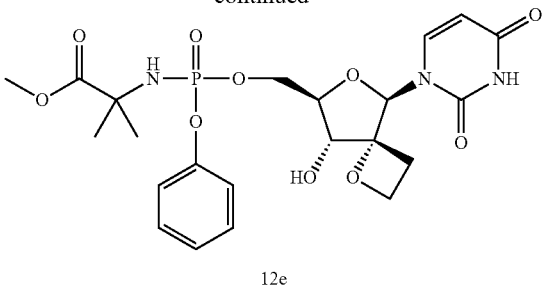

To a solution of 10 (1.0 eq., 0.28 mmol, 75 mg) in dry THF (3 mL) was added 1-methylimidazole (NMI; 12.0 eq., 3.33 mmol, 0.27 mL) at room temperature. A solution of intermediate 11 (1.4 eq., 0.39 mmol, 0.43 mL) was added dropwise and the mixture was stirred at room temperature for 1 hour. The reaction mixture was washed three times with 0.5 M HCl. The organic layer was dried over MgSO$_4$ and concentrated in vacuo. The residue was purified by column chromatography on silica gel (0-10% methanol in CH$_2$Cl$_2$) to give compound 12e (24 mg, yield=15%, purity=95%) as a mixture of diastereomers. HPLC Condition A; Rt: 1.49 min, m/z=526 (M+H)$^+$. $^1$H NMR (400 MHz, DMSO-d$_6$) δ ppm 1.33 (s, 3H), 1.37 (s, 3H), 2.42-2.43 (m, 2H), 3.56 (s, 3H), 3.70-3.79 (m, 1H), 3.80-3.88 (m, 0.4; H), 3.88-3.96 (m, 0.6; H), 4.09-4.20 (m, 1H), 4.26-4.48 (m, 3H), 5.50-5.56 (m, 1H), 5.61-5.69 (m, 1H), 5.88-5.97 (m, 1H), 5.97-6.04 (m, 1H), 7.12-7.24 (m, 3H), 7.31-7.41 (m, 2H), 7.44 (d, J=8.22 Hz, 0.4H), 7.52 (d, J=8.02 Hz, 0.6H), 11.49 (br. s., 1H).

Example 9

Using a similar procedure as outlined above, the following compounds were prepared. In each case analysis was done on mixtures of diastereomers.

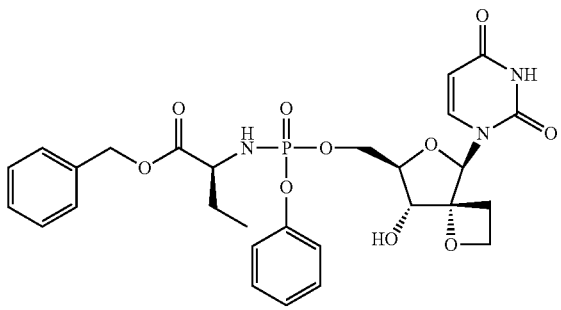

HPLC Condition A Rt: 2.00 min, m/z=602 (M+H)$^+$; $^1$H NMR (400 MHz, DMSO-d$_6$) δ ppm 0.71-0.83 (m, 3H), 1.45-1.73 (m, 2H), 2.33-2.48 (m, 2H), 3.59-3.80 (m, 2H), 3.79-3.96 (m, 1H), 4.04-4.19 (m, 1H), 4.24-4.47 (m, 3H), 4.98-5.14 (m, 2H), 5.47-5.57 (m, 1H), 5.58-5.73 (m, 1H), 5.96-6.03 (m, 1H), 5.96-6.03 (m, 1H), 7.09-7.22 (m, 3H), 7.27-7.39 (m, 7H), 7.44 (d, J=8.02 Hz, 0.5H), 7.48 (d, J=8.22 Hz, 0.5H), 11.50 (br. s., 1H).

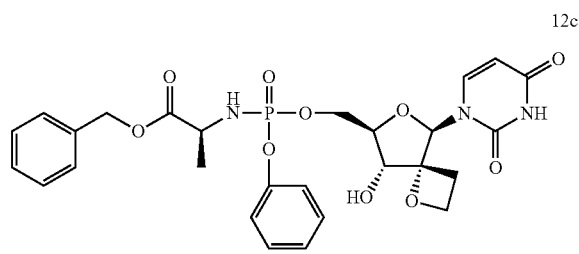 [SMILES: C[C@H](NP(=O)(OC[C@H]1O[C@@H](n2ccc(=O)[nH]c2=O)[C@@]2(CCO2)[C@@H]1O)Oc1ccccc1)C(=O)OCc1ccccc1]

12c

HPLC Condition A; Rt: 1.92 min, m/z=588 (M+H)⁺; ¹H NMR (400 MHz, DMSO-d₆) δ ppm 1.19-1.29 (m, 3H), 2.38-2.46 (m, 2H), 3.53-3.97 (m, 3H), 4.06-4.20 (m, 1H), 4.26-4.46 (m, 3H), 5.05-5.14 (m, 2H), 5.49-5.59 (m, 1H), 5.61-5.73 (m, 1H), 5.88-6.05 (m, 1H), 6.07-6.18 (m, 1H), 7.09-7.23 (m, 3H), 7.30-7.40 (m, 7H), 7.43-7.51 (m, 1H), 11.51 (br. s., 1H).

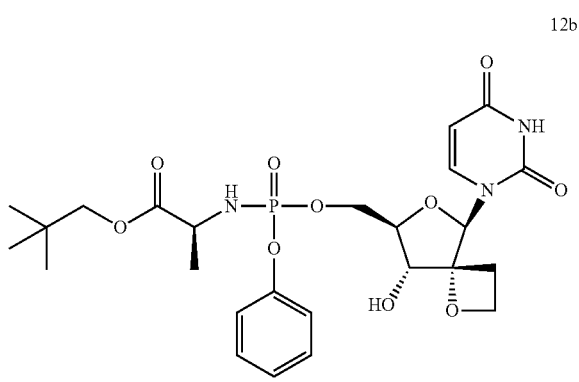 [SMILES: C[C@H](NP(=O)(OC[C@H]1O[C@@H](n2ccc(=O)[nH]c2=O)[C@@]2(CCO2)[C@@H]1O)Oc1ccccc1)C(=O)OCC(C)(C)C]

12b

HPLC Condition A Rt: 2.00 min, m/z=568 (M+H)⁺; ¹H NMR (400 MHz, DMSO-d₆) δ ppm 0.79-0.93 (m, 9H), 1.20-1.32 (m, 3H), 2.33-2.50 (m, 2H), 3.63-3.70 (m, 1H), 3.71-3.80 (m, 2H), 3.80-3.93 (m, 2H), 4.04-4.21 (m, 1H), 4.23-4.46 (m, 3H), 5.49-5.59 (m, 1H), 5.58-5.72 (m, 1H), 5.94-6.03 (m, 1H), 6.02-6.14 (m, 1H), 7.11-7.25 (m, 3H), 7.32-7.39 (m, 2H), 7.41-7.53 (m, 1H), 11.51 (br. s., 1H).

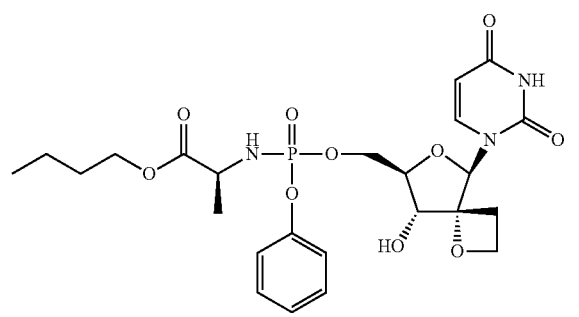

12a

HPLC Condition A, Rt: 1.88 min, m/z=554 (M+H)⁺; ¹H NMR (400 MHz, DMSO-d₆) δ ppm 0.77-0.93 (m, 3H), 1.14-1.25 (m, 3H), 1.24-1.37 (m, 2H), 1.41-1.62 (m, 2H), 2.35-2.47 (m, 2H), 3.63-3.92 (m, 3H), 3.92-4.06 (m, 3H), 4.05-4.21 (m, 1H), 4.23-4.46 (m, 3H), 5.48-5.59 (m, 1H), 5.59-5.72 (m, 1H), 5.89-6.15 (m, 2H), 7.09-7.25 (m, 3H), 7.31-7.41 (m, 2H), 7.43-7.52 (m, 1H), 11.51 (br. s., 1H)

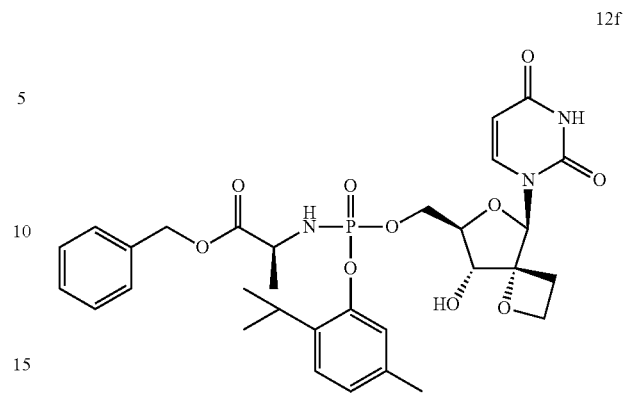

12f

HPLC Condition A, Rt: 3.46 min, m/z=644 (M+H)⁺ ¹H NMR (400 MHz, DMSO-d₆) δ ppm 11.37-11.61 (1H, m) 7.40-7.46 (1H, m) 7.27-7.39 (5H, m) 7.09-7.19 (2H, m) 6.89-6.96 (1H, m) 6.07-6.20 (1H, m) 5.98-6.03 (1H, m) 5.58-5.72 (1H, m) 5.45-5.52 (1H, m) 5.02-5.15 (2H, m) 4.23-4.45 (3H, m) 4.05-4.18 (1H, m) 3.82-3.98 (2H, m) 3.69-3.78 (1H, m) 3.13-3.26 (1H, m) 2.37-2.47 (2H, m) 2.15-2.23 (3H, m) 1.24-1.32 (3H, m) 1.06-1.15 (6H, m)

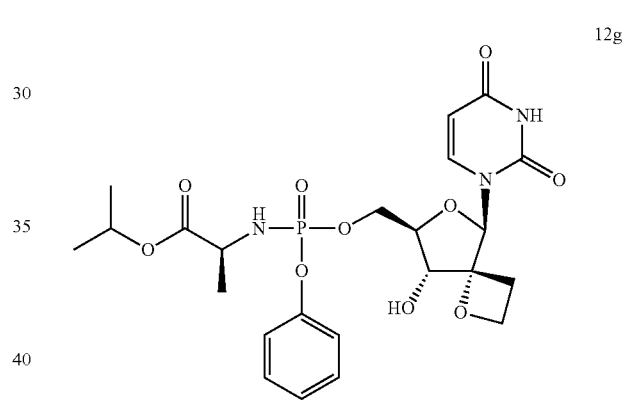

12g

HPLC Condition A, Rt: 2.08 & 2.21 min (individual diastereomers seen), m/z=540 (M+H)⁺, ¹H NMR (400 MHz, DMSO-d₆) δ ppm 11.39-11.60 (1H, m) 7.44-7.52 (1 H, m) 7.31-7.40 (2H, m) 7.12-7.24 (3H, m) 5.95-6.07 (2H, m) 5.59-5.71 (1H, m) 5.51-5.58 (1H, m) 4.78-4.91 (1H, m) 4.26-4.44 (3H, m) 4.06-4.20 (1H, m) 3.84-3.95 (1H, m) 3.68-3.83 (2H, m) 2.37-2.58 (2H, m) 1.16-1.25 (3H, m) 1.11-1.16 (6H, m)

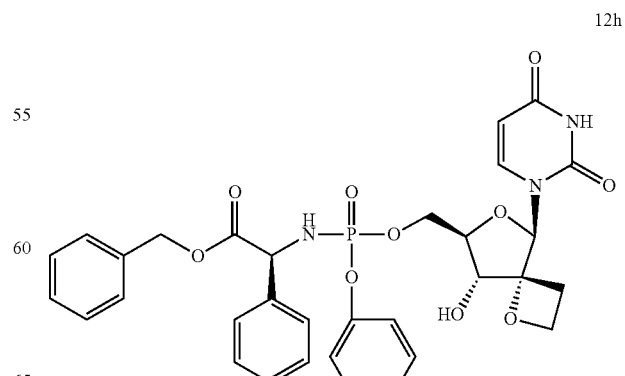

12h

HPLC Condition A, Rt: 3.03 min, m/z=650 (M+H)⁺. ¹H NMR (400 MHz, DMSO-d₆) δ ppm 11.34-11.62 (1H, m) 7.05-7.46 (16H, m) 6.71-6.84 (1H, m) 5.95-6.03 (1H, m) 5.56-5.71 (1H, m) 5.46-5.53 (1H, m) 4.95-5.16 (3H, m) 4.23-4.45 (3H, m) 4.05-4.21 (1H, m) 3.77-3.88 (1H, m) 3.68-3.77 (1H, m) 2.35-2.45 (2H, m)

12i

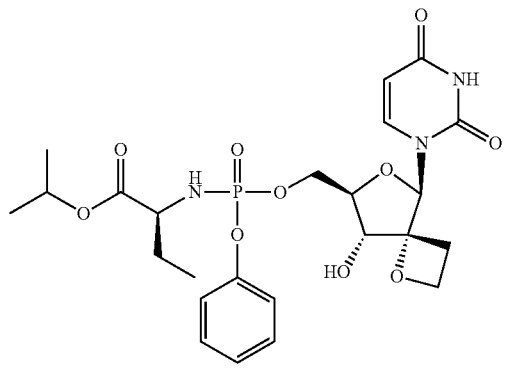

HPLC Condition A, Rt: 2.38 & 2.48 min (individual diastereomers seen), m/z=554 (M+H)⁺, ¹H NMR (400 MHz, DMSO-d₆) δ ppm 11.38-11.61 (1H, m) 7.43-7.53 (1 H, m) 7.31-7.41 (2H, m) 7.11-7.25 (3H, m) 5.90-6.06 (2H, m) 5.59-5.71 (1H, m) 5.50-5.59 (1H, m) 4.79-4.93 (1H, m) 4.27-4.46 (3H, m) 4.03-4.21 (1H, m) 3.82-3.95 (1H, m) 3.68-3.81 (1H, m) 3.52-3.66 (1H, m) 2.38-2.51 (2H, m) 1.44-1.72 (2H, m) 1.09-1.21 (6H, m) 0.72-0.89 (3H, m)

12j

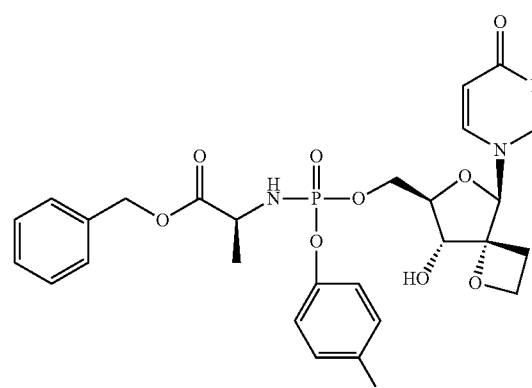

HPLC Condition A, Rt: 2.84 & 2.94 min (individual diastereomers seen), m/z=622 (M+H)⁺, ¹H NMR (400 MHz, CDCl₃) δ ppm 1.38 (d, J=8.59 Hz, 3H), 2.38-2.57 (m, 1H), 2.66-2.84 (m, 1H), 3.25 (br. s., 1H), 3.78 (br. s., 1H), 3.81-3.94 (m, 1H), 3.95-4.15 (m, 2H), 4.23-4.42 (m, 1H), 4.42-4.58 (m, 2H), 4.60-4.72 (m, 1H), 5.14 (s, 2H), 5.68 (d, J=8.00 Hz, 1H), 6.07 (s, 0H), 7.01-7.19 (m, 2H), 7.20-7.43 (m, 7H), 8.76 (br. s., 1H)

12k

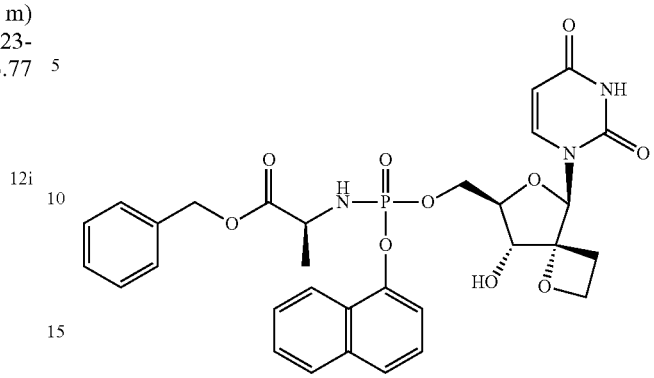

HPLC Condition A, Rt: 3.06 min, m/z=638 (M+H)⁺. ¹H NMR (400 MHz, CDCl₃) δ ppm 1.23-1.41 (m, 2H), 1.66 (br. s., 0H), 1.93 (br. s., 1H), 2.37 (m, J=12.56, 12.56, 8.63, 6.24 Hz, 1H), 2.54-2.75 (m, 1H), 3.44-3.67 (m, 1H), 3.78 (dd, J=9.27, 1.85 Hz, 1H), 3.86-4.03 (m, 1H), 4.05-4.17 (m, 1H), 4.18-4.28 (m, 1H), 4.31-4.41 (m, 1H), 4.41-4.66 (m, 3H), 4.96-5.16 (m, 2H), 5.32 (d, J=8.20 Hz, 0H), 5.44 (d, J=8.20 Hz, 0H), 6.11 (s, 1H), 7.08 (d, J=8.19 Hz, 0H), 7.18-7.41 (m, 6H), 7.44-7.57 (m, 3H), 7.64 (d, J=8.00 Hz, 1H), 7.78-7.89 (m, 1H), 8.01-8.18 (m, 1H), 9.37 (br. s., 1H)

12l

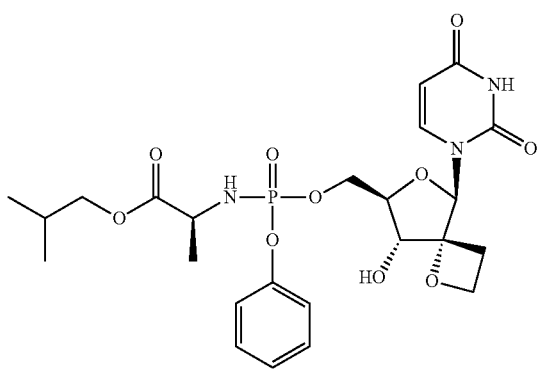

HPLC Condition A, Rt: 2.48 & 2.59 min (individual diastereomers seen), m/z=554 (M+H)⁺. ¹H NMR (400 MHz, CDCl₃) δ ppm 0.92 (d, J=5.46 Hz, 5H) 1.28-1.45 (m, 2 H) 1.48-2.02 (m, 2H) 2.38-2.56 (m, 1H) 2.64-2.87 (m, 1H) 3.67-4.17 (m, 5H) 4.28-4.58 (m, 2H) 4.66 (br. s., 1H) 5.60-5.70 (m, 1H) 6.19 (s, 1H) 7.10-7.49 (m, 6H) 8.56 (br. s., 1H)

12m

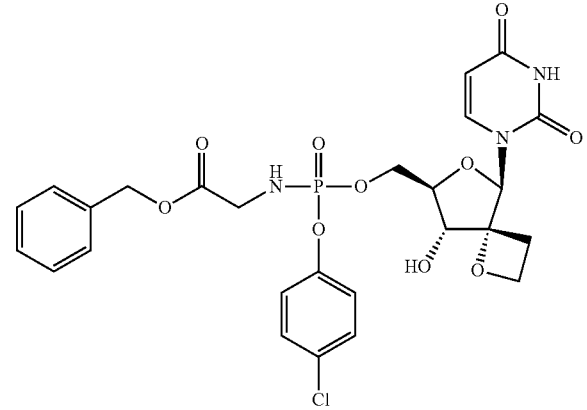

HPLC Condition A, Rt: 2.61 min, m/z=608 (M+H)⁺. ¹H NMR (400 MHz, CDCl₃) δ ppm 2.40-2.56 (m, 1H), 2.67-2.82 (m, 1H), 3.29 (br. s., 1H), 3.71-3.97 (m, 4H), 3.97-4.10 (m, 1H), 4.32-4.44 (m, 1H), 4.45-4.59 (m, 2H), 4.61-4.70 (m, 1H), 5.16 (s, 2H), 5.68 (d, J=7.80 Hz, 1H), 6.10 (d, J=6.44 Hz, 1H), 7.10-7.19 (m, 2H), 7.24-7.30 (m, 3H), 7.30-7.42 (m, 5H), 8.82 (br. s., 1H)

Biological Examples

Replicon Assay

The compounds of formula I were examined for activity in the inhibition of HCV-RNA replication in a cellular assay. The assay was used to demonstrate that the compounds of formula I inhibited a HCV functional cellular replicating cell line, also known as HCV replicons. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an internal ribosome entry site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV genotype 1b. Continued culture of the replicon cells in the presence of G418 (neo$^R$) is dependent on the replication of the HCV-RNA. The stably transfected replicon cells that express HCV-RNA, which replicates autonomously and to high levels, encoding inter alia luciferase, were used for screening the antiviral compounds.

The replicon cells were plated in 384-well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC$_{50}$ values were then calculated, which value represents the amount of the compound required to decrease the level of detected luciferase activity by 50%, or more specifically, the ability of the genetically linked HCV replicon RNA to replicate.

Results

Table 1 shows the replicon results (EC$_{50}$, replicon) and cytotoxicity results (CC$_{50}$ (μM) (Huh-7)) obtained for compounds of the examples given above. Also the HIV activity is given (EC$_{50}$ HIV (μM)) and the cellular toxicity in the HIV cell-line (CC$_{50}$ (μM) (MT-4)).

| Compound number | EC$_{50}$ (μM) (HCV) | CC$_{50}$ (μM) (Huh-7) | EC$_{50}$ (μM) (HIV) | CC$_{50}$ (μM) (MT4) |
|---|---|---|---|---|
| 12a | 3.4 | >98 | >98 | >98 |
| 12b | 3.7 | >98 | >98 | >98 |
| 12c | 5.6 | >98 | >98 | >98 |
| 12d | 5.5 | >98 | >98 | >98 |
| 12e | 23.4 | >98 | >98 | >98 |
| 12f | 8.7 | 18.7 | >98 | 1.3 |
| 12g | 17.8 | >98 | >98 | >98 |
| 12h | 79.64 | >88 | >98 | >98 |
| 12i | >96 | >98 | >98 | >98 |
| 12j | 0.7 | >98 | >98 | >98 |
| 12k | 2.0 | >98 | >76.9 | >98 |
| 12l | 0.44 | >98 | >98 | >98 |
| 12m | 7.17 | >98 | >98 | >98 |

The invention claimed is:

1. A compound of formula I:

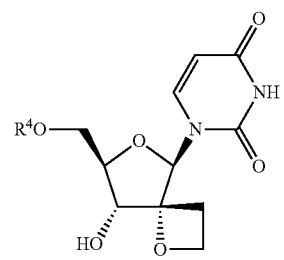

(I)

including any possible stereoisomers thereof, wherein:

$R^4$ is a monophosphate, diphosphate or triphosphate ester; or $R^4$ is a group of formula

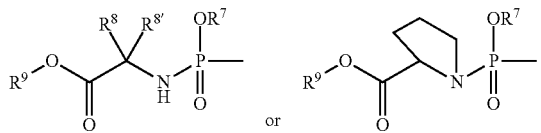

$R^7$ is phenyl, optionally substituted with 1, 2, or with 3 substituents each independently selected from halo, $C_1$-$C_6$alkyl, $C_3$-$C_6$alkenyl, $C_1$-$C_6$alkoxy, hydroxy, and amino; or $R^7$ is naphthyl, optionally substituted with 1, 2, or with 3 substituents each independently selected from halo, $C_1$-$C_6$alkyl, $C_3$-$C_6$alkenyl, $C_1$-$C_6$alkoxy, hydroxy, and amino; or $R^7$ is indolyl, optionally substituted with one $C_1$-$C_6$alkyloxy-carbonyl group and optionally further with 1, 2, or with 3 substituents each independently selected from halo, $C_1$-$C_6$alkyl, $C_3$-$C_6$alkenyl, $C_1$-$C_6$alkoxy, hydroxy, and amino;

$R^8$ is hydrogen, $C_1$-$C_6$alkyl, benzyl, or phenyl;

$R^{8'}$ is hydrogen, $C_1$-$C_6$alkyl, benzyl, or phenyl; or $R^8$ and $R^{8'}$ together with the carbon atom to which they are attached form $C_3$-$C_7$cycloalkyl;

$R^9$ is $C_1$-$C_{10}$alkyl, $C_3$-$C_7$cycloalkyl or phenyl-$C_1$-$C_6$alkyl, wherein the phenyl moiety in phenyl or phenyl-$C_1$-$C_6$alkyl is optionally substituted with 1, 2 or 3 substituents each independently selected from hydroxy, $C_1$-$C_6$alkoxy, amino, mono- and di$C_1$-$C_6$alkylamino;

or a pharmaceutically acceptable salt or solvate thereof.

2. A compound according to claim 1, wherein $R^4$ is a group of formula

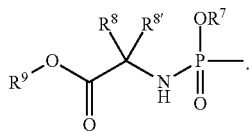

3. A compound according to claim 1, wherein $R^7$ is phenyl, optionally substituted with halo or with one or two $C_1$-$C_6$alkyl groups, or $R^7$ is naphthyl or indolyl.

4. A compound according to claim 1, wherein $R^7$ is phenyl, optionally substituted with halo, or with two $C_1$-$C_6$alkyl groups, or $R^7$ is naphthyl.

5. A compound according to claim 1, wherein $R^7$ is phenyl or naphtyl.

6. A compound according to claim 1, wherein $R^8$ is hydrogen, and $R^{8'}$ is hydrogen or $C_1$-$C_6$alkyl.

7. A compound according to claim 1, wherein $R^8$ is hydrogen and $R^{8'}$ is methyl or ethyl.

8. A compound according to claim 1, wherein $R^9$ is $C_1$-$C_6$alkyl or benzyl.

9. A compound according to claim 1, wherein $R^9$ is n.butyl or benzyl.

10. A compound which is:

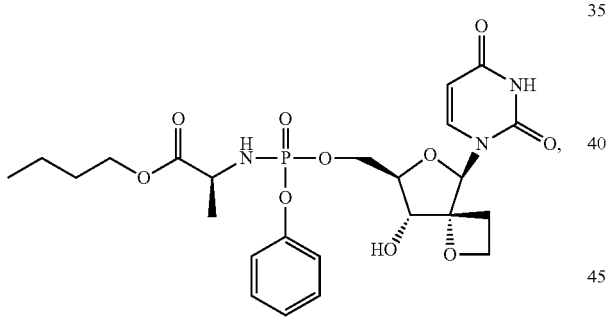

12a

12c

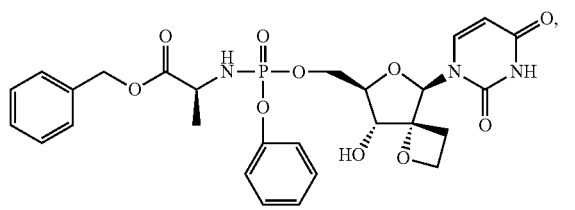

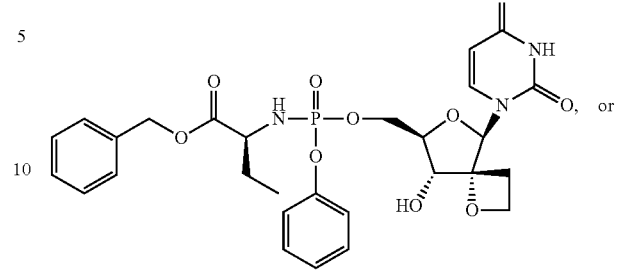

12d

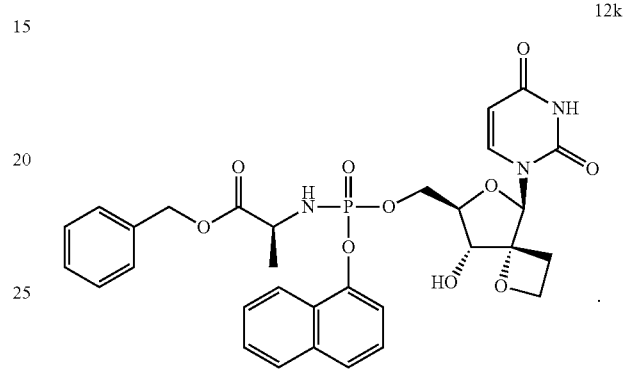

12k

11. A pharmaceutical composition comprising an anti-virally effective amount of a compound of claim 1 and a pharmaceutically acceptable carrier.

12. A method for inhibiting HCV, comprising administering to a patient in need thereof an effective amount of a compound of claim 1.

13. A compound according to claim 10 which is:

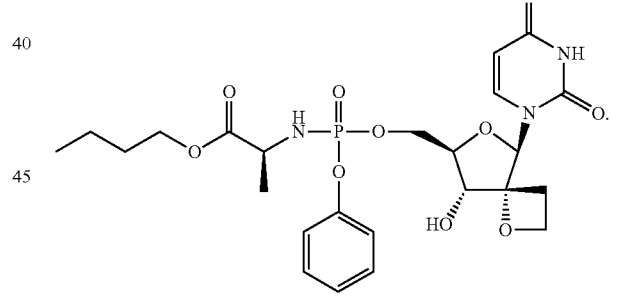

12a

14. A pharmaceutical composition comprising an anti-virally effective amount of a compound of claim 13 and a pharmaceutically acceptable carrier.

15. A method for inhibiting HCV, comprising administering to a patient in need thereof an effective amount of a compound of claim 13.

* * * * *